United States Patent [19]

Davison

[11] Patent Number: 4,735,606
[45] Date of Patent: Apr. 5, 1988

[54] CHEST DRAINAGE APPARATUS

[75] Inventor: Thomas W. Davison, Chesterfield, Mo.

[73] Assignee: Sherwood Medical Company, St. Louis, Mo.

[21] Appl. No.: 433,932

[22] Filed: Oct. 12, 1982

[51] Int. Cl.⁴ .......................... A61F 2/60; A61F 2/80
[52] U.S. Cl. ...................................... 604/28; 604/45; 604/35; 604/118; 604/246; 604/321
[58] Field of Search ........................ 604/23, 26, 27, 30, 604/31, 28, 35–38, 43, 45, 321, 51, 318, 246, 34, 73, 118, 129, 250, 280, 246, 119; 137/205

[56] References Cited

U.S. PATENT DOCUMENTS

| | | | |
|---|---|---|---|
| 2,230,218 | 2/1941 | Asche | 604/43 |
| 2,470,665 | 5/1949 | Stiehl | 128/276 |
| 2,568,566 | 9/1951 | Sokolik | 128/240 |
| 2,614,563 | 10/1952 | Devine, Jr. | 128/276 |
| 2,727,678 | 12/1955 | Henderson | 230/69 |
| 3,066,672 | 12/1962 | Crosby, Jr. et al. | 128/276 |
| 3,085,573 | 4/1963 | Meyer et al. | 128/240 |
| 3,142,298 | 7/1964 | Koski et al. | 604/31 |
| 3,208,145 | 9/1965 | Turner | 32/33 |
| 3,375,828 | 4/1968 | Sheridan | 128/351 |
| 3,395,705 | 8/1968 | Hamilton | 128/276 |
| 3,416,532 | 12/1968 | Grossman | 604/45 |
| 3,626,928 | 12/1971 | Barringer et al. | 604/38 |
| 3,628,532 | 12/1971 | Magrath . | |
| 3,749,090 | 7/1973 | Stewart | 128/240 |
| 3,810,471 | 5/1974 | Truhan | 128/276 |
| 3,889,675 | 6/1975 | Stewart | 604/34 |
| 3,982,540 | 9/1976 | Ross | 128/278 |
| 4,036,210 | 7/1977 | Campbell et al. | 128/2 F |
| 4,049,000 | 9/1977 | Williams | 604/119 |
| 4,300,550 | 11/1980 | Gandi et al. | 604/26 |
| 4,363,321 | 12/1982 | Chittenden | 604/34 |
| 4,372,336 | 2/1983 | Cornell et al. | 137/205 |
| 4,382,442 | 5/1983 | Jones | 604/35 |

FOREIGN PATENT DOCUMENTS

| | | | |
|---|---|---|---|
| 2454308 | 12/1980 | France | 604/43 |
| 2079609 | 1/1982 | United Kingdom | 604/45 |

OTHER PUBLICATIONS

*The Journal of Thoracic and Cardiovascular Surgery*, vol. 78, No. 1, Jul. 1979, pp. 119–122, Beaudet M.D.
Axiom Medical Inc., Paramount, CA. 90723, "A Sump that Works".

Primary Examiner—C. Fred Rosenbaum
Assistant Examiner—H. Macey
Attorney, Agent, or Firm—Stanley N. Garber; Andrew J. Beck; William R. O'Meara

[57] ABSTRACT

A medical underwater seal, chest drainage apparatus is provided which includes a catheter having a main lumen and an auxiliary lumen for insertion into a chest cavity to be drained of body fluid. The main lumen is connected to a drainage collection device and the auxiliary lumen is adapted to be connected to a variable setting venting valve so that an adjustable flow rate of air from the atmosphere can flow into the auxiliary lumen for venting the cavity.

15 Claims, 1 Drawing Sheet

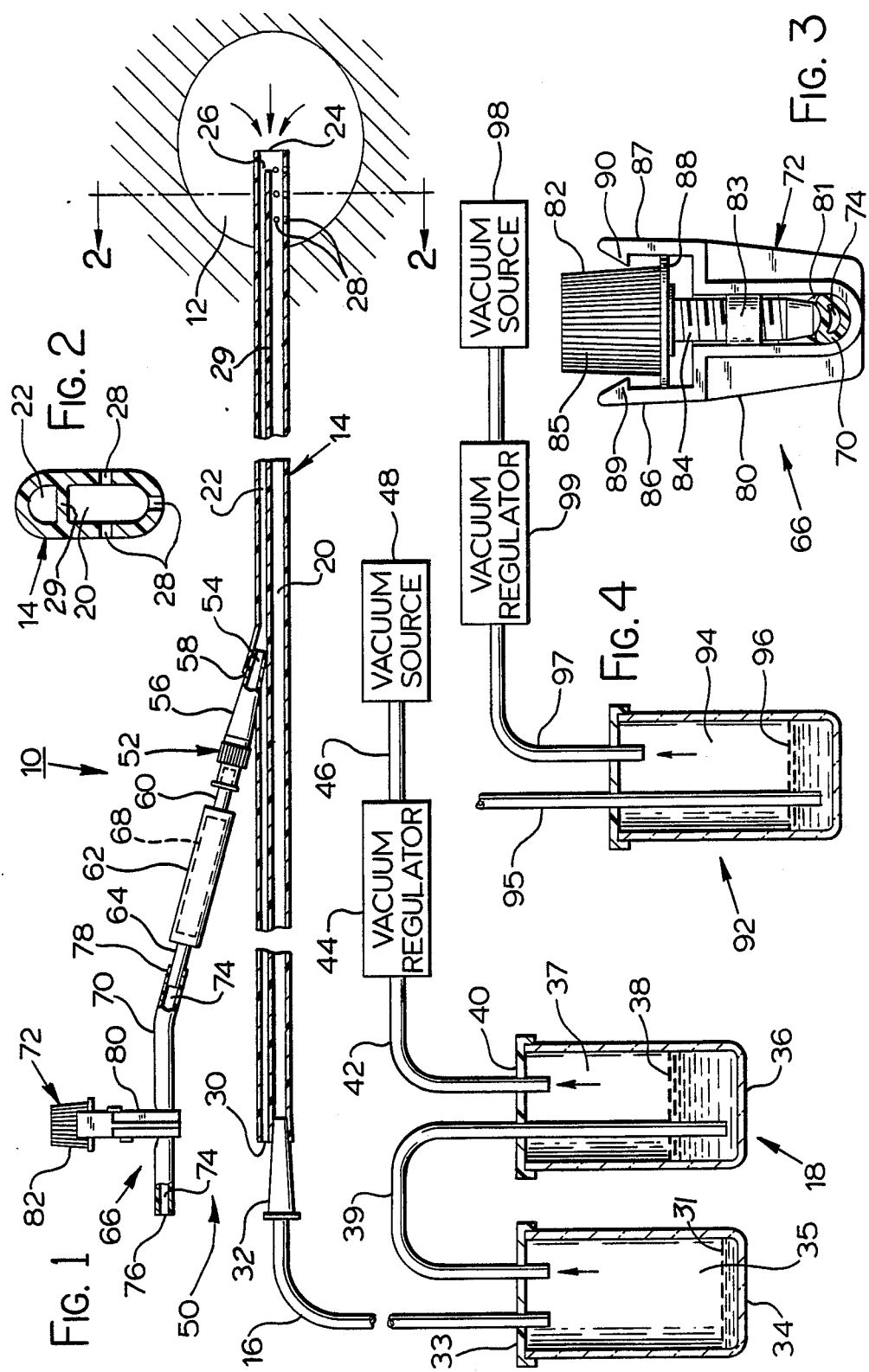

CHEST DRAINAGE APPARATUS

TECHNICAL FIELD

This invention relates to chest wound drainage apparatus and more particularly to chest wound drainage apparatus which provides venting of the body cavity to be drained.

BACKGROUND ART

In draining fluid from a body cavity or wound to promote healing, such as after chest surgery, a catheter and a drain tube are usually connected to drain the fluid into a drainage collection system either by the force of gravity alone or with the assistance of suction. Usually, the system includes an underwater seal "bottle" or chamber in series with a source of suction. In closed cavity or wound drainage systems where there is no air leak or air flowing into the cavity, drainage fluid flows from the cavity as the walls of the cavity tend to approximate or come together. Once the walls substantially approximate, the system tends to become static with the pressure in the cavity becoming substantially equal to the underwater seal collection system pressure, even though drainage fluids may remain in the catheter and drain tube, and even some in the cavity. Also, blood clots may clog the catheter such that fluids no longer readily drain into the underwater seal collection system but tend to build up in the catheter and/or drain tube.

In order to restore proper drainage in a static system, it is sometimes necessary to vent the body cavity thereby providing the force necessary to remove drainage fluids. One method of venting the cavity has been to clamp off the catheter and disconnect it from the drain tube. After reconnection, air in the tube reduces the negative pressure in the cavity. This procedure requires time and effort on the part of the attendant or nurse and may allow bacteria to enter the cavity. In an attempt to provide some filtering, cloth or the like has been placed over the open end of the tube. Another method is to discontinue the suction and introduce filtered air through a hypodermic needle and filter, for example, by inserting a needle into the drain tube and allowing air to enter the system and reduce the pressure in the cavity. Disconnecting the drain tube and the use of a filtered needle, of course, are unhandy methods and only provide a given amount of air at a time. Also, these methods may have to be repeated several times during a drainage collection procedure.

It is also common practice to strip the drain tube in order to pull blood and clots in the wound space into the collection tubing. This stripping is done by hand squeezing the tube and moving the hand toward the underwater seal collection system. This can, however, result in excessive negative pressures being applied to the cavity. Such excessive negative pressures may damage delicate tissues, cause excessive drainage and make drainage less efficient as the higher negative pressures pull tissues into and clot catheter eyes. In order to reduce the negative pressures to the desired value in the chest wound after stripping, air has been introduced into the cavity by the undesirable methods mentioned above.

Multi-lumen catheters have been used in which one of the lumens is connected to the atmosphere through a filter to vent the body cavity. However, depending upon the flow rate of air into the cavity, such air flows through the catheter drainage tube and bubbles through the usual underwater seal of the chest drainage suction system and this can result in excessive evaporation of the seal. Such venting does not provide a controlled degree of venting or controlled negative pressures in the cavity, and does not allow adjustment of the amount of air bubbling through the underwater seal. Uncontrolled or an excessive amount of gas bubbling into the underwater seal increases the risk that the seal will fail and allow the reverse passage of gas back to the body cavity. Also, the usual stripping of the drainage tube in order to obtain momentary high negative pressures in the cavity so as to remove clots from the eyes of the catheter is not possible where relatively high air flow venting of the cavity is provided.

SUMMARY OF THE INVENTION

It is an object of the present invention to provide improved chest wound suction drainage apparatus wherein bubbling and evaporation of liquid of an underwater seal can be controlled while adequate negative pressures can be employed, wherein removal of blood clots and debris can more easily be accomplished while eliminating or reducing the amount of tube stripping, and wherein venting of the cavity can be readily temporarily stopped so that stripping can be done effectively when necessary, and wherein one or more of the above problems or disadvantages of past drainage arrangements are overcome.

In accordance with one aspect of the present invention, a chest wound drainage apparatus is provided which includes main and auxiliary catheter lumens for placement in a body cavity to be drained of body fluid, a chest drainage collection device for connection in fluid communication with the main lumen and which includes an underwater seal, and an air venting device for controllably venting the cavity to the atmosphere which includes an adjustable member connected to control the rate of flow of air from the atmosphere to the auxiliary lumen.

These, as well as other objects and advantages of the present invention, will become apparent from the following detailed description and accompanying drawing.

BRIEF DESCRIPTION OF THE DRAWING

FIG. 1 is a somewhat schematic illustration, partly in cross-section, showing a preferred embodiment of a chest wound drainage apparatus in accordance with the present invention;

FIG. 2 is a cross-sectional view taken along line 2—2 of FIG. 1;

FIG. 3 is a side elevational view, on an enlarged scale, of the body cavity venting valve of the apparatus of FIG. 1; and FIG. 4 shows an alternate form of suction drainage collection apparatus that can be used with the catheter of FIG. 1.

DETAILED DESCRIPTION OF THE PREFERRED EMBODIMENT

Referrring now to the drawings, and more particularly to FIG. 1, a chest wound suction drainage apparatus 10 is shown connected to drain body fluid from a body cavity indicated at 12. Apparatus 10 is shown including a catheter 14 connected by a drain tube 16 to an underwater seal, suction drainage collection device indicated generally at 18.

Catheter 14, as seen also in FIG. 2, has a main or drainage lumen 20 and an auxiliary or body cavity vent lumen 22, both lumens being open at a distal end 24 of the catheter. Preferably, the distal end of vent lumen 22, as indicated at 26, is proximally spaced from the distal end 24 of the catheter so that the distal end of the vent lumen will remain open even if the distal end of the catheter is closed by body tissue or blood clots. The distal end portion of catheter 14 is provided with a plurality of drainage eyes or openings 28 which extend through the catheter sidewall and connect with the drainage lumen 20.

The catheter 14 may be made of a suitable rubber or plastic, for example, it may be extruded from a suitable thermoplastic material such as polyvinyl chloride or a silicone rubber. The lumens 20 and 22 are formed in the same catheter with a longitudinally extending integral wall 29 separating the lumens. Where desired, the catheter 14 may be formed by two separate catheters, one having a drainage lumen and the other having a vent lumen, and with the distal ends of the catheters disposed adjacent to each other within the body cavity when in use.

The drainage lumen 20 is open at the proximal end 30 of the catheter and receives a tube coupler 32 which is also connected to one end of drain tube 16. The other end of tube 16 sealingly extends through a lid 33 of a drainage collection container or bottle 34 of the drainage collection device 18. Container 34 has a collection chamber 35 for receiving drainage fluid including gas or air and liquid such as indicated at 31. Tube 16 extends only a short distance below the bottom side of lid 33, that is, to a point near the top of chamber 35 and which is above the level of the maximum quantity of drainage liquid to be received by the chamber. The bottom end of drain tube 16 provides the drainage inlet of the collection chamber 35.

Collection device 18 also includes an underwater seal or liquid seal container or bottle 36, having an underwater seal or a liquid seal chamber 37 which, in use, is provided with a predetermined quantity of liquid or water, such as indicated at 38. A tube 39 also sealingly passes through lid 33 of the collection container 34 and extends only a short distance below the bottom side of lid 33. The left end portion of tube 39, as viewed in FIG. 1, is near the top of chamber 35 and serves as the gas outlet of the collection container 34. Tube 39 sealingly extends also through a lid 40 of the underwater seal 36 and extends below the upper level of the liquid or water 38 to a point close to the bottom of chamber 37. A tube 42 sealingly extends through lid 40 to a point just below the lid and which is above the liquid 38. Tube 42 extends to a vacuum regulator 44 which, in turn, is connected by a tube 46 to a vacuum source 48 which may be a conventional hospital vacuum source. The vacuum regulator 44 may be a well-known or conventional liquid suction control "bottle" which employs water or other liquid to limit the negative pressure applied to the underwater seal chamber 37 and collection container 35. As is well known, varying the height of the liquid in a control bottle varies the maximum negative pressure at the collection chamber. Where desired, regulator 44 may be an adjustable mechanical vacuum regulator or controller, such as shown and disclosed in co-pending application Ser. No. 160,447, filed June 17, 1980, now U.S. Pat. No. 4,372,336, and which has the same assignee as this application. Where the chambers of the chest unit used are integrally formed, integral passages can be used to connect such chambers in fluid communication instead of employing separate tubes such as tubes 39 and 42. The underwater seal collection device 18 may be any of various suitable, well-known or commercially available chest drainage units. The containers 34 and 36 are preferably of transparent glass or plastic so that liquids in them can be seen.

Drainage apparatus 10 further includes an adjustable flow, body cavity air venting device indicated generally at 50. The venting device 50 is shown including a connector 52 having an air flow passage or lumen 54 and an outer tapered wall 56, preferably having a friction surface. The narrow end of the tapered connector 52 is shown inserted into an opening 58 in the side wall of catheter 14 that connects with the auxiliary lumen 22. The connector 52 is inserted until there is a tight sealing fit with the opening 58, that is, so that air cannot escape between the outer surface of connector 52 and the opening 58, and such that the connector closes lumen 22 except for passage 54. The free end of connector 52 is sealingly connected to an air outlet 60 of an air filter member 62 having an air inlet 64 connectable to the atmosphere through an ajustable or variable air flow venting valve 66. Filter member 62 may contain a suitable air filtering material 68 such as porous cellulose or polysulfone. Preferably, the filter material 68 is one that prevents bacteria from passing through it but allows sufficient air flow for body cavity venting purposes.

The venting valve 66 may be any suitable type of valve that will provide an adjustable or selectively variable resistance to air flow through the valve and, preferably, a valve that is also capable of closing off air flow through it for reasons which will be discussed hereafter. Valve 66 is shown including a resiliently collapsible tube 70 connected to the inlet 64 of air filter 62, and a manually adjustable venting valve member 72, shown as an adjustable clamp on tube 70. Tube 70 has a passage or lumen 74 which is open to the atmosphere at the left or proximal end 76 and which end serves as the valve inlet. Passage 74 extends through the valve member 72 with a right end 78 serving as the valve outlet. With this arrangement, when the valve 66 is open, air can flow into the valve inlet 76 of tube 70, through the valve 66, through the air filter 62, through connector 52, and into the vent lumen 22 of catheter 14. Tube 70 may be made of any suitable material such as rubber or plastic, for example, extrudable polyvinyl chloride. Preferably, tube 70 is pliable or flexible enough to close and resilient enough to open from a closed condition, and can be repeatably opened and closed.

As best seen in FIG. 3, the adjustable valve member 72 includes a valve housing 80 having an adjustable opening 81 through which tube 70 extends, and a manually adjustable valve control member 82. Housing 80 has an internally threaded, laterally extending integral portion 83 above opening 81 which threadedly receives a threaded portion 84 of valve control member 82. Member 82 has a head 85 which is manually grasped for turning the valve control member 82. The housing 80 also has a pair of diametrically opposed arms 86 and 87 which extend upwardly and frictionally engage an outer flange 88 on head 85 to maintain the threaded member 84 in a desired adjusted position or setting. The arms also have abutments 89 and 90, respectively, which limit excessive axial upward movement of control member 82 to prevent separation of the control member from housing 80.

When the control member 82 is rotated in one direction, the bottom end of threaded portion 84 engages the upper side of tube 70 to compress it, such as shown in FIG. 3, and to reduce the effective cross-section of the tube or size of passage 74 at that point, thereby increasing the flow resistance and reducing the rate of flow of air through the passage 74 of valve tube 70. When it is adjusted in this direction (downwardly), to a maximum degree, the tube 70 is completely compressed and its passage 74 is closed, and no air can flow through it. When the control member 82 is rotated in the opposite direction, the resiliency of the tube 70 causes the tube passage 74 to increase in size or cross-section to thereby reduce the resistance to air flow through the tube 70. In this way, the control member 82 can be adjustably rotated to selectively vary the effective size or cross-sectional area of passage 74 at the valve member 72 to effect a selected flow resistance to air flow from the atmosphere to the vent lumen 22 and cavity 12.

The drainage apparatus 10 is especially useful in draining body fluid from closed wounds or cavities such as in a mediastinal drainage system. In such a case, the body cavity 12 would be the mediastinum. The apparatus 10 is also advantageously used for pleural or thoracic cavity drainage even where there may be an air lead through the lung or through the stitching since the amount of venting is adjustable. Apparatus 10 is especially advantageous when the pleural cavity becomes closed as the patient heals.

In describing the operation of the apparatus 10, it will be assumed that the body cavity 12 is the mediastinum cavity of a patient and that the distal end portion of catheter 14 is placed adjacent a wound or surgical incision in the cavity 12. Generally, the catheter extends from the wound through a separate opening formed in the chest wall to the exterior of the chest, this opening being in air-tight relation with the outer wall of the catheter. The proximal end of the main or drainage lumen 20 of catheter 14 is connected securely to drain tube 16, such as by the connector 32. With the underwater seal drainage collection device 18 connected and operating with a predetermined vacuum in the liquid seal chamber 37, a negative pressure is applied to the cavity 12 through tube 39, collection chamber 35, the drain tube 16, and drainage lumen 20 of catheter 14. Preferably, the adjusting valve member 82 is adjustably rotated to allow some air to flow into the vent lumen 22 of catheter 14, and then into the cavity 12. Air or gas and liquid from the cavity flow through the drainage lumen 20, drain tube 16, and into collection chamber 35. Gas flows from drain tube 16 into chamber 35, into the collection outlet or tube 39, as indicated by the arrow, and into the liquid 38 in liquid seal chamber 37 where it bubbles up through the liquid. Gas rising from liquid 38 flows into the underwater seal outlet or tube 42, as indicated by the arrow, to the vacuum regulator 44, and then into the vacuum source 48. Drainage liquid 31, of course, accumulates in collection chamber 35.

The flow of air from the atmosphere to the cavity can be adjusted to provide a desirable pressure differential between the pressures in the cavity 12 and suction collection chamber 35 so as to move drainage fluid, if any, from the cavity 12 even after the walls of the cavity have collapsed about the catheter 14. During normal drainage conditions, the venting valve 66 is preferably adjusted so that there is a slight bubbling of air in the liquid seal chamber 37 and this bubbling can be readily adjusted during drainage, in this case, by simply turning valve control member 82 in one or the opposite direction. If the valve 66 is open too much, that is, so as to allow a high rate of flow of gas or air into the vent lumen 22, excessive bubbling through the liquid seal may occur which causes an undesirable rate of evaporation of the seal liquid 38. This increases the chance that, eventually, the level of liquid 38 will fall below the bottom of tube 39 and the underwater seal will become ineffective. However, since valve 66 can be readily adjusted, bubbling through the liquid seal can be controlled or limited for various settings of the vacuum or suction force of the regulator 44. Thus, bubbling in the liquid seal and the pressures within the cavity can be readily adjusted during drainage of the body cavity under various operating conditions and without necessarily adjusting regulator 44.

During drainage operations, if a condition occurs in which the open end 24 and openings 28 of the catheter 14 become clogged or partially clogged, for example, by invagination of tissue and/or blood clots, even though some venting of the cavity is being employed, the valve 66 can be re-adjusted to momentarily increase the rate of flow of air from the atmosphere to vent lumen 22 and the cavity 12. This tends to free tissues from the catheter openings and to increase the forces tending to move the clogging drainage matter toward the collection chamber 35 and without the necessity of increasing the negative pressure supplied by the vacuum regulator 44. After the drainage matter that caused the clogging has passed into collection chamber 35, the valve 66 may be again adjusted, for example, to return it to its originally adjusted condition in order to reduce the rate of flow of air into the catheter 14 and thereby reduce the amount of bubbling and evaporation of liquid 38 in liquid seal chamber 37. This operation and reduction in bubbling and evaporation of liquid 38 is, of course, accomplished without the necessity of changing the setting of vacuum regulator 44.

Should the increase of air flow into the vent lumen 22 fail to dislodge the material clogging the catheter openings or otherwise fail to result in the desired drainage fluid flow, hand stripping of the catheter 14 or drain tube 16 can be performed without creating high negative pressures in the body cavity that may be harmful to the patient. This is accomplished by stripping with the valve 68 opened to a significant degree or fully opened. In general, it is, of course, desirable to avoid producing excessive negative pressure in the cavity since such pressures tend to increase the amount of drainage fluid, for example, by causing hemorrhaging of small blood vessels. Thus, in this way, stripping can be performed while the pressure in the cavity is close to atmospheric pressure rather than at an excessively high negative pressure.

If tissue and/or drainage matter clogs the openings 28 and open end of the catheter 14, and increasing the rate of flow of air into the vent lumen 22 by adjusting valve control member 72 as mentioned above does not dislodge the drainage matter, stripping of the catheter 14 or drain tube 16 can be employed, if desired, with the valve closed to stop the ventilation of the lumen 22. The catheter 14 or drain tube 16 can be stripped in this manner to create a momentary high negative pressure in the drainage lumen 20 which may move the drainage matter and eliminate the clogging. After such stripping, the valve 66 is adjusted to again provide cavity venting and lower the negative pressure in the cavity.

While the underwater seal drainage collection device 18 is shown in FIG. 1 for illustration as including two liquid bottles or containers 34 and 36, other well-known forms of suction underwater seal drainage collection devices can be used with the catheter 14 and adjustable venting device 50. For example, in FIG. 4, a modified drainage collection system 92 is shown which includes a combined collection and liquid seal chamber 94. A drain tube 95, which is adapted to be connected to the catheter 14 of FIG. 1 in the same manner as drain tube 16, passes through the lid of chamber 94 and extends into a liquid 96. An outlet tube 97 has its lower end in the upper portion of the container 94 and is connected to a vacuum source 98 through a vacuum regulator 99 to provide the upper portion of the chamber 94 with the desired negative pressure for draining fluid from a body cavity. In this case, an initial amount of liquid 96 provides an initial liquid seal and the drainage liquid from drain tube 95 mixes with the initial amount of liquid. Gas from the drain tube 95 bubbles through the liquid in chamber 94 and enters the outlet tube 97 as indicated by the arrow. Controlling the bubbling in this underwater seal system to a relatively low level decreases the amount of foaming experienced when air bubbles through bloody drainage. Venting valve device 50 may be operated with suction collection system 92 in a manner similar to that described in connection with the collection system 18 of FIG. 1.

The venting valve 66 allows fine adjustments in the rate of flow of air to the vent lumen 22 and cavity, and is steplessly or smoothly variable from a closed condition where no air from the atmosphere flows into lumen 22 from the valve to condition of maximum rate of flow of air into the lumen 22. This allows good venting control under various operating conditions such as pointed out herein.

The valve 66 is formed of essentially rigid parts except for the tube 70. The housing 80 and control member 82 may be formed or molded economically from a relatively rigid or hard plastic, for example, polycarbonate or the like, so that the apparatus 10 can be disposable or economically discarded after use with a single patient. Other types of adjustable valves, for example, conventional ball and ramp type clamp valves for adjustably closing tubing are also usable. Air flow control valves other than clamp type valves are, of course, also usable.

The adjustable venting valve 66 and catheter 14 are especially desirable where commonly used underwater seals are employed in the body fluid collection system, since the bubbling of air through the liquid seal can be readily smoothly and repeatedly controlled or adjusted during drainage operations, reducing the chance of excessive evaporation. Valve 66 can be repeatably adjusted and returned to any given flow resistance setting within its operating range to provide good control over the amount of bubbling in the underwater seal.

As various changes could be made in the above construction without departing from the scope of the invention, it is intended that all matter contained in the above description or shown in the accompanying drawings shall be interpreted as illustrative and not in a limiting sense.

I claim:

1. A chest drainage apparatus comprising catheter means having main and auxiliary lumens adapted for placement adjacent a wound in a chest cavity to be drained of body fluid, suction drainage collection means for connection in fluid communication with said main lumen and a source of suction for effecting a negative pressure in said main lumen and for receiving body drainage fluid from the body cavity, said collection means including container means having means for holding a liquid to provide an underwater seal between said main lumen and the source of vacuum and whereby gas from said main lumen bubbles through said liquid, and variable flow air vent means adapted for connection in fluid communication with said auxiliary lumen and the atmosphere for controllably venting the body cavity to the atmosphere, said vent means including a manually adjustable valve for selectively varying the resistance to the flow of air from the atmosphere to said auxiliary lumen to permit adjustment of the amount of bubbling of gas in said liquid when the apparatus is in use, said valve being adjustable to selectively effect different flow resistances between the maximum and minimum flow resistances of the operating range of said valve.

2. The apparatus of claim 1 wherein said adjustable valve is selectively adjustable to close off fluid communication between the atmosphere and said auxiliary lumen.

3. The apparatus of claim 1 wherein said adjustable valve is adjustable to vary the resistance to the air flow from the atmosphere to said auxiliary lumen in a stepless manner.

4. The apparatus of claim 1 wherein said container means includes a first chamber adapted for connection with said main lumen for receiving gas and liquid from said main lumen, a second chamber for holding a selected quantity of liquid, passage means for connecting said first chamber at a point above any liquid therein to a point in said second chamber below the level of liquid therein when the selected quantity of liquid is in said second chamber, and means for connecting said second chamber at a point above the level of the selected quantity of liquid to a source of suction.

5. The apparatus of claim 4 wherein said vent means includes a resilient, flexible tube connected to said auxiliary lumen and having one end open to the atmosphere, and said adjustable valve comprises an adjustable clamp for compressing said tube and selectively varying the size of the lumen of said tube at said valve.

6. The apparatus of claim 5 wherein said clamp includes a threaded member threadedly adjustable to vary the size of the lumen of said tube at said clamp.

7. The apparatus of claim 4 wherein said valve includes a manually adjustable valve member adjustable to control the resistance to the flow of air to said auxiliary lumen in a substantially stepless manner and adjustable to a closed position in which no air passes through said valve to said auxiliary lumen.

8. The apparatus of claim 4 further including filter means for filtering air from the atmosphere to said auxiliary lumen.

9. The apparatus of claim 4 wherein said catheter means includes plastic tubing and said main and auxiliary lumens extend longitudinally along said tubing and are separated by an integral wall of said tubing.

10. A chest drainage apparatus comprising a catheter with drainage and vent lumens each having one end adapted for placement in chest cavity adjacent a wound to be drained of body fluid and the other end of each disposed externally of the chest, drainage collection means including a drainage collection chamber for receiving drainage fluid from the body cavity up to a predetermined level therein, and an underwater seal chamber having a selected quantity of liquid therein, a drain tube connected between said other end of said drainage lumen and said collection chamber, first passage means having one end connected in fluid communication with said collection chamber above said predetermined level of liquid and the opposite end at a point below the level of said selected quantity or liquid in said underwater seal chamber, means for connecting a source of regulated suction to said underwater seal chamber at a point above the level of said selected quantity of liquid whereby gas from said drainage lumen during operation of the apparatus bubbles through said selected quantity of liquid to said suction source connecting means, and manually controllable vent means for venting the body cavity to the atmosphere including means for providing an air flow passage form the atmosphere to said auxiliary lumen, and a manually adjustable valve connected in series in said air flow passage for varying the effective flow resistance of said air flow passage whereby the pressure differential between the pressures in the cavity and collection chamber is controllable and the bubbling of gas through said selected quantity of liquid is controllable to limit evaporation thereof when the apparatus is in use, said valve being adjustable to selectively effect different flow resistances between the maximum and minimum flow resistances of the operating range thereof.

11. The apparatus of claim 10 wherein valve member is adjustable to vary said flow resistance in a stepless manner.

12. The apparatus of claim 10 wherein said valve is adjustable to close said air flow passage.

13. The apparatus of claim 10 further including a filter connected in series flow relation with said valve and vent lumen.

14. The method of drainiang body fluid from a wound in a chest cavity comprising the steps of positioning catheter means having a drainage lumen and a vent lumen in the cavity adjacent a wound, connecting the drainage lumen to a chest drainage colletion device for receiving the body fluid and which has an underwater seal connected to receive gas from the drainage lumen and which has a liquid through which the gas bubbles, connecting a source of suction to the underwater seal to receive the gas bubbling from the liquid in the underwater seal, providing an air flow passage from the atmosphere to the vent lumen of the catheter and an adjustable air flow valve member for controlling the rate of flow of air through the passage, said valve being adjustable to effect selection of any one of different flow resistances between the maximum and minimum flow resistances of the operating range of the valve, and adjusting the rate of flow of air to the vent lumen such that during drainage of body fluid air bubbling through the underwater seal is at a manually controlled rate.

15. The method of claim 14 wherein said valve is adjsutable in a stepless manner.

* * * * *